United States Patent [19]

Cavazza

[11] Patent Number: 5,037,851

[45] Date of Patent: Aug. 6, 1991

[54] USE OF ACETYL L-CARNITINE IN THE THERAPEUTIC TREATMENT OF CATARACT, AND PHARMACEUTICAL COMPOSITIONS USEFUL IN SUCH TREATMENT

[75] Inventor: Claudio Cavazza, Rome, Italy

[73] Assignee: Sigma-Tau Industrie Farmaceutiche Riunite S.p.A., Rome, Italy

[21] Appl. No.: 436,203

[22] Filed: Nov. 14, 1989

[30] Foreign Application Priority Data

Nov. 15, 1988 [IT]  Italy ................. 48558 A/88

[51] Int. Cl.$^5$ .................... A61K 31/205; A61K 31/22
[52] U.S. Cl. .................... 514/556; 514/551; 514/912
[58] Field of Search .............. 514/556, 913, 551

[56] References Cited

FOREIGN PATENT DOCUMENTS 0225856 10/1985  European Pat. Off. ............ 514/564

Primary Examiner—Frederick E. Waddell
Assistant Examiner—Zohreh A. Fay
Attorney, Agent, or Firm—Oblon, Spivak, McClelland, Maier & Neustadt

[57] ABSTRACT

The use is described of acetyl L-carnitine and its pharmacologically acceptable salts in the therapeutic treatment of cataract. The medicament may be administered orally or parenterally or be applied as a collyrium containing approximately 10%-15% w/v of acetyl L-carnitine.

1 Claim, No Drawings.

USE OF ACETYL L-CARNITINE IN THE THERAPEUTIC TREATMENT OF CATARACT, AND PHARMACEUTICAL COMPOSITIONS USEFUL IN SUCH TREATMENT

BACKGROUND OF THE INVENTION

Field Of Invention:

This invention concerns a new therapeutic application of acetyl L-carnitine and its pharmacologically acceptable salts in the therapeutic treatment of cataract. The invention further concerns suitable pharmaceutical compositions and particularly a collyrium.

Discussion Of The Background:

Therapeutic uses of acetyl L-carnitine are already known For example, U.S. Pat. No. 4,194,006 describes the use of acetyl carnitine in the therapeutic treatment of ischemia and myocardial arrhythmia. U.S. Pat. No. 4,343,816 describes the use of acetyl carnitine in the therapeutic treatment of functional peripheral vascular diseases of the arteries, such as Raynaud's disease and acrocyanosis. U.S. Pat. No. 4,346,107 describes the therapeutic utility of acetyl carnitine in the treatment of subjects affected by altered cerebral metabolism which is found for example in senile and pre-senile dementia and in Alzheimer's disease. However there is no correlation between the previously known therapeutic uses of acetyl L-carnitine and that which forms the subject of this invention. Moreover, the therapeutic use has never previously been proposed in the ophtamological field of either carnitine or of any derivative of carnitine.

SUMMARY OF THE INVENTION

It has now surprisingly been discovered that the use of acetyl L-carnitine and its pharmacologically acceptable salts is effective in the therapeutic treatment of cataract. More particularly, it has been found that acetyl L-carnitine and its pharmacologically acceptable salts are useful in the treatment of senile and pre-senile degenerative cataract, of diabetic cataract, of juvenile cataract, and of cataract which has hereditary metabolic causes or nutritional causes, or develops as a result of poisoning or inflammation This invention accordingly contemplates the use of acetyl L-carnitine and its pharmacologically acceptable salts to produce a pharmaceutical composition for the therapeutic treatment of cataract.

DETAILED DESCRIPTION OF THE PREFERRED EMBODIMENTS

In practice, approximately 1000 to 2000 mg daily of acetyl L-carnitine or an equivalent quantity of one of its pharmacologically acceptable salts is administered orally or parenterally. Alternatively, or preferably at the same time as the oral or parenteral treatment, a collyrium is administered containing 10–15% w/v of acetyl L-carnitine or an equivalent quantity of its pharmacologically acceptable salts. The collyrium is applied to the extent of 2-3 drops 3-4 times daily.

The pharmaceutical compositions most suitable for oral or parenteral administration ar the compositions which in the form of a single dose, contain approximately 500 to approximately 1000 mg of acetyl L-carnitne or of one of its pharmacologically acceptable salts and a pharmacologically acceptable excipient that is compatible with the active component. Example of suitable compositions in the form of a single dose are described in, for example, U.S. Pat. No. 4,464,393.

The compositions for the collyrium comprise the usual sterile isotonic solutions. The choice of the suitable excipients is within the capabilities of a normally skilled person in pharmaceutical technology. For example, use is made of excipient such as sodium chloride, dibasic sodium phosphate, monobasic potassium phosphate, benzalkonium chloride, and ethyl alcohol. The composition is brought to the correct volume with distilled water.

The activity of acetyl L-carnitine in combating cataract has been demonstrated both by mean of pharmacological tests in experimental models in vivo and in vitro and in clinical studies. Some of such tests in experimental models are described below.

1. Experimental models of cataract in vivo.

The counteracting effects of acetyl L-carnitine on the onset of cataract were evaluated using the following experimental models of in vivo cataract.

Rabbits of the New Zealand breed were used, weighing approximately 2 kg, and also female rats of Wistar breed, weighing approximately 45–55 g. After being suitably housed at room temperature (21° C.), and with a predetermined lightness/darkness cycle (lighting provided between 08:00h and 20:00h) the animals were kept on the special diets indicated below. Water was freely available.

(a) Diet without tryptophane

The rabbits were kept on a synthetic diet without tryptophane for a period of 30 days. The appearance of opacity at the lens occurred after about 30 days from the start of the treatment.

(b) Hypergalactosemic diet

The rats were kept on a diet constituted as to 50% by galactose and as to the remaining 50% by standard fodder, for a period of 30 days. The appearance of mature cataract was observed after the twentieth day.

By means of a slit lamp the various ocular segments were checked: conjuctiva, cornea, anterior chamber, iris, crystalline lens. The site and the extent of the lenticular opacity were tested, using the following parameters:

0: absence of opacity
+: initial occurrence of lenticular opacity
++: presence of diffused opacity
+++: lens wholly covered by cataract 2. Experimental model of cataract in vitro.

The effects of acetyl L-carnitine on the cataract of the rats (female Wistar rats weighing approximately 45–55 g) in vitro were evaluated using the following experimental model.

Each crystalline lens, after extraction, was incubated in a medium containing 5,55 mM of glucose and 15% of fetal calf serum, which caused the development of lenticular opacity after about 96 hours;

3. Results (a) In the experimental model of the tryptophane-free cataract in rabbits, 20 rabbits were used, of which 10 were treated with a physiologic solution and 10 with acetyl L-carnitine (LAC) administered topically by instillations into the conjuctival sac of on to two drops three times daily of a collyrium of 10% acetyl L-carnitine. The animals were treated with acetyl L-carnitine from the start of the medicated diet. The animals treated with acetyl L-carnitine displayed a degree of protection with regard to the progress of the cataract formation when compared to the control animals.

(b) In the experimental model of the galactosemic cataract in rats, 20 rats were used, of which 10 were treated with a physiologic solution and 10 with acetyl L-carnitine, administered topically by means of instillations of a collyrium of 10% acetyl L-carnitine into the conjuctival sac at the rate of one to two drops three times daily. The animals were treated with acetyl L-carnitine from the start of the medicated diet. The animals treated with acetyl L-carnitine displayed a degree of protection with regard to the progress of the cataract formation when compared to the control animals. Evaluation of the efficacy of the acetyl L-carnitine was carried out by means of periodic checks using a slit lamp and supported by photographic records.

(c) In the in vitro cataract experimental model, 5 groups of 10 crystalline lenses of rats were used. One was incubated in a medium without medicaments, and the others incubated in a medium containing graduated concentrations of acetyl L-carnitine ($1 \times 10^{-10}$, $1 \times 10^{-8}$, $1 \times 10^{-6}$M) and/or sorbinil (inhibitor of aldose reductase, $1 \times 10^{-10}$, $1 \times 10^{-8}$, $1 \times 10^{-6}$ and $1 \times 10^{-4}$M). The treatment established a degree of protection that was dosage-dependent with regard to the formation of cataracts in vitro, strengthening the anti-cataract-inducing effect of the sorbinil. At a concentration of $1 \times 10^{-8}$ of the two medicaments the formation of cataract proved to be completely inhibited.

What is claimed:

1. A therapeutic method for the treatment of cataract which comprises administering orally or parenterally to a subject having a cataract 1000 to 2000 mg/day of acetyl L-carnitine or an equivalent quantity of one of its pharmacologically acceptable salts.

* * * * *